United States Patent [19]

Pontagnier et al.

[11] Patent Number: 4,818,772

[45] Date of Patent: Apr. 4, 1989

[54] DERIVATIVES OF 4-AMINOETHOXY-5-ISOPROPYL-2-METHYLBENZENES: METHODS OF SYNTHESIS AND UTILIZATION AS MEDICINES

[75] Inventors: Henri Pontagnier; Christian Courtiol, both of Pessac; Marie-Hélène Creuzet, Bourdeaux; Claude Feniou, Pessac; Gisèle Prat, Talence, all of France

[73] Assignee: Societe Cortial S.A., Paris, France

[21] Appl. No.: 366,133

[22] Filed: Apr. 9, 1982

[30] Foreign Application Priority Data

Jun. 4, 1981 [FR] France ................. 81 06832
Apr. 3, 1982 [FR] France ................. 82 03795
Apr. 3, 1982 [FR] France ................. 82 03796

[51] Int. Cl.$^4$ ............................ A61K 31/135
[52] U.S. Cl. ......................... 514/651; 549/362; 514/101; 514/540; 564/353; 564/354
[58] Field of Search .......... 424/316, 330; 560/20, 560/209, 131, 142, 250; 564/353, 354; 549/362

[56] References Cited

U.S. PATENT DOCUMENTS

| | | | |
|---|---|---|---|
| 2,688,638 | 9/1954 | Gump et al. | 564/354 |
| 2,688,639 | 9/1954 | Gump et al. | 564/354 |
| 3,192,253 | 6/1965 | Boscott et al. | 564/354 X |
| 3,341,572 | 9/1967 | Engelhard et al. | 564/354 X |
| 3,816,516 | 6/1974 | Cox et al. | 564/353 X |
| 3,988,475 | 10/1976 | Manghisi et al. | 564/354 X |
| 4,147,805 | 4/1979 | Morrow et al. | 564/354 X |
| 4,336,396 | 6/1982 | Giordano et al. | 564/354 X |

OTHER PUBLICATIONS

Wagner et al., "Synthetic Organic Chemistry", pp. 155, 567 and 660 (1963).

Primary Examiner—Robert V. Hines
Attorney, Agent, or Firm—Oblon, Fisher, Spivak, McClelland & Maier

[57] ABSTRACT

A compound with alpha 1-blocking activity having the formula:

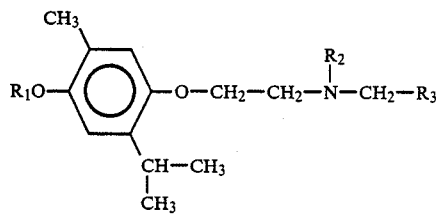

wherein $R_1$ is —H, —$CH_3$ or —$COCH_3$; $R_2$ is —H or $CH_3$; and $R_3$ is

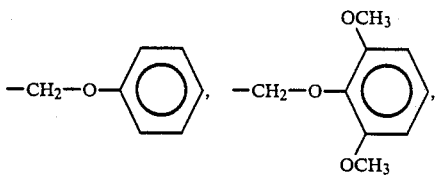

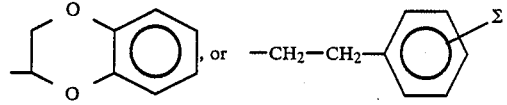

wherein $\Sigma$ is —H or one or more substituents selected from the group consisting of halogen, —OH and —$OCH_3$; or a pharmaceutically acceptable salt thereof.

4 Claims, No Drawings

DERIVATIVES OF 4-AMINOETHOXY-5-ISOPROPYL-2-METHYL-BENZENES: METHODS OF SYNTHESIS AND UTILIZATION AS MEDICINES

The present invention relates to new compounds that exhibit alpha-blocking activity and which act to prevent the aggregation of platelets. It also relates to methods for the synthesis of these compounds, to pharmaceutical formulations that contain them, and to their therapeutic applications.

These compounds have the general formula

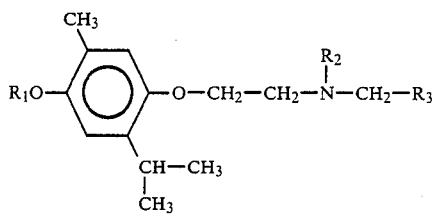

In this formula $R_1 = H, -CH_3, -COCH_3$ $R_2 = H, CH_3$

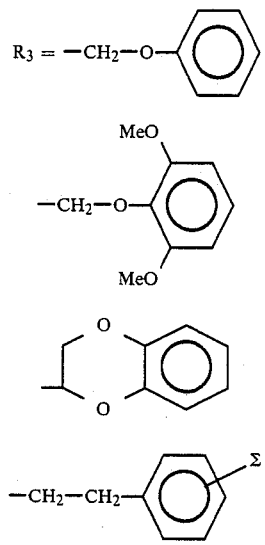

with $\Sigma = H$ or one or more substituents such as OH, OCH$_3$, or halogen.

The new compounds are prepared as free bases or as pharmaceutically acceptable salts, for example, as adducts with inorganic acids (hydrochloric, hydrobromic, sulfuric, phosphoric) or organic acids (citric, methanesulfonic, camphorsulfonic).

The class of medicines that exhibits alpha-blocking activity consists of derivatives that act on presynaptic receptors (or alpha 2 receptors) such as yohimbine, derivatives thaft act specifically on postsynaptic receptors (or alpha 1 receptors) such as moxisylyte and prazosin, and derivatives that act simultaneously on pre- and postsynaptic receptors such as phentolamine. Derivatives that possess specifically a postsynaptic, alpha-blocking activity are of special interest because they bring about a decrease in the peripheral resistance of arteries and veins without producing the undesirable, secondary effects exhibited by derivatives with dual alpha 1 and alpha 2 activity (cardiac intolerance, tachycardia). Currently, alpha 1-blocking derivatives such as prazosin are utilized mostly in the treatment of hypertension, cardiac insufficiency, and vasomotor difficulties of the limbs. In view of the presence of alpha receptors in a large number of organs, we can envision the utilization of alpha-blocking agents in the treatment of angina to alleviate coronary spasms, in the prevention of thromboembolic phenomena, and, in combination with a beta stimulant, in the treatment of asthma attacks.

The products in the present invention are derived from the formula of moxisylyte.

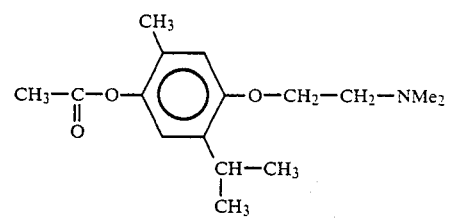

They differ from moxisylyte mainly by the substitution on the nitrogen atom of a second chain containing an aromatic ring. H. Kapur and D. R. Mottram (J. Pharm. Pharmacol., 1975, 27, 295 and Biochem. Pharmacol., 1978, 27, 1879) have described similary compounds such as WB4101

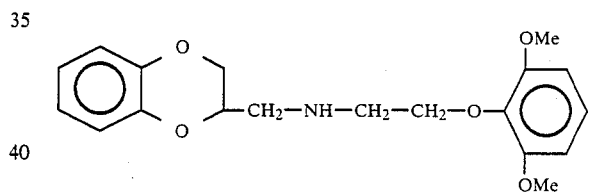

The compounds of the present invention exhibit, when compared with known alpha-blocking compounds, an alpha 1 blocking activity of longer duration as well as a lesser toxicity. Moreover, they act to prevent the aggregation of platelets, and thus these compounds may be utilized in the prevention or treatment of thrombosis.

The compounds in the present invention are synthesized from 5-isopropyl-2-methyl-4-N-methylaminoethoxyphenol through intermediate compounds of formula I with $R_1 = H$ and $R_2 = CH_3$. This phenol reacts with the acid chloride derived from $R_3COOH$, where $R_3$ represents the groups defined above, to produce

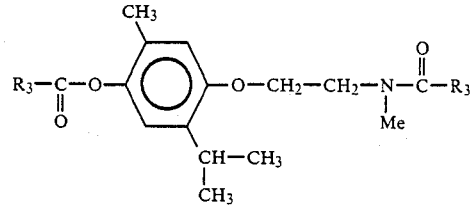

This derivative is reduced with LiAlH$_4$ to give

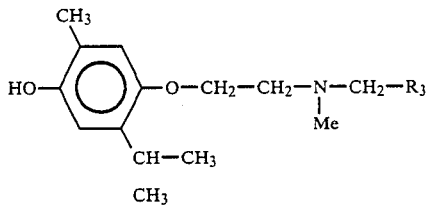

Derivatives with $R_1 = CH_3$ or $COCH_3$ are obtained via the classic methylation and acetylation reactions or phenolic OH. The derivatives with $R_2 = H$ are produced in two steps. In the first step, reaction with BrCN yields a cyanamide, and this is followed by reduction with $LiAlH_4$ to yield the desired product.

The invention will be described in more detail in the following examples. However, it must be noted that the examples provided do not limit the scope of the invention.

EXAMPLE 1

Synthesis of 5-isopropyl-2-methyl-4-(N-methyl-N-phenoxyethylaminoethoxy)-phenol (formula I with $R_1 = H$,

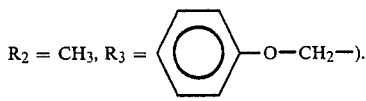

To a solution of 20.5 g of 5-isopropyl-2-methyl-4-N-methylaminoethoxyphenol in a mixture of 200 ml of benzene and 27 ml of triethylamine is added dropwise a solution of 36 g of phenoxyacetyl chloride in 100 ml of benzene. The mixture is heated for 2 hours. The benzene is removed by evaporation and the resulting residue is treated with 2N HCl. The residue is extracted twice with 100 ml of chloroform. The chloroform phase is washed and dried. The chloroform is removed by evaporation. A compound of formula

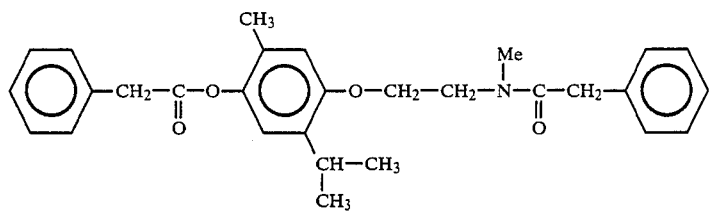

is obtained in 44 g yield.

12.5 g of $LiAlH_4$ is suspended in 500 ml of ethyl ether. 79 g of the above compound dissolved in 350 ml of ethyl ether is added dropwise to the suspension of $LiAlH_4$. The resulting mixture is refluxed for 3 hours, and then allowed to cool. The excess $LiAlH_4$ is decomposed by treatment with an aqueous saturated solution of $Na_2SO_4$. The resulting solution is acidified by adding a solution of sulfuric acid. The aqueous phase is made basic by adding a solution of ammonia to a pH of 9. In this manner, 48 g of the compound of Example 1 is obtained.

EXAMPLE 2

Synthesis of N-methyl-N-phenoxyethyl-2-[(2-isopropyl-4-methoxy-5-methyl)phenoxy]ethylamine (formula I with $R_1 = CH_3$, $R_2 = CH_3$, $R_3 =$ 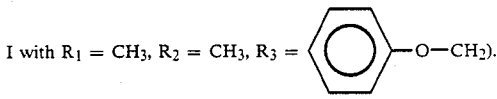

Small amounts of diazomethane are added at room temperature and with stirring to a solution of 21 g of the product of Example 1 in 200 ml of ethyl ether. The presence of excess diazomethane is controlled by means of acetic acid. The progress of the reaction is followed by analytical HPLC under the following conditions: column, μ Bondapack C18; eluant, methanol 65 ml/water 35 ml/Pic B7 1 dose/liter; flow rate, 2 ml/minute; detection, UV at 280 nm; k' of starting material, 0.9; k' of final product, 3. When the methylation reaction is complete, the excess diazomethane is decomposed by slow addition of acetic acid. After purification, 15 g of the compound of Example 2 is obtained.

EXAMPLE 3

Synthesis of the hydrochloride of N-methyl-N-phenoxyethyl-2-[(2-isopropyl-4-methoxy-5-methyl)-phenoxy]ethylamine or COR 28 09.

5 g of the product of Example 2 is dissolved in 100 ml of ethyl ether. After cooling, gaseous HCl is bubbled through the solution. The resulting hydrochloride is filtered and washed with ether. The product is obtained in 5.2 yield and has a melting point of 97° C.

EXAMPLE 4

Synthesis of N-phenoxyethyl-2-[(2-isopropyl-4-methoxy-5-methyl)phenoxy]ethylamine (formula I with

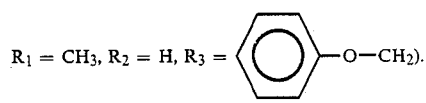

11.2 g of the product of Example 2 dissolved in 200 ml of benzene at room temperature is added dropwise to a solution of 3.5 g of BrCN in 10 ml of benzene. The progress of the reaction is followed by analytic HPLC according to the following conditions: column, μ Bondapack C 18; eluant, methanol 65 ml/water 35 ml/Pic B7 1 dose/liter; flow rate, 2 ml/minute; detection, UV at 280 nm, k' of initial reactant 3; k' of final product 6.5. When the reaction is complete, the benzene is removed by evaporation in a rotary evaporator, and the resulting residue is treated with 15 ml of 2N HCl. The insoluble material is extracted with ethyl ether. The ether phase is washed, dried, and evaporated. One obtained 7 g of the derivative chloroform is removed by evaporation. One obtains in this manner 63 g of

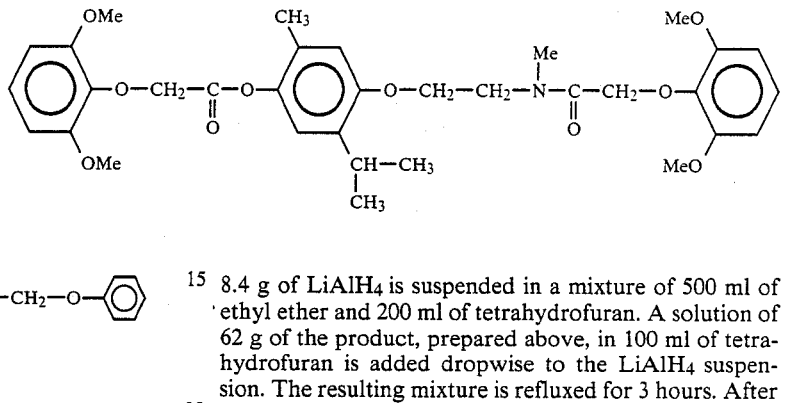

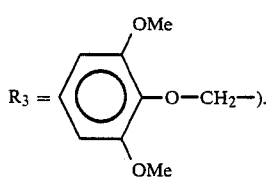

1.5 g of LiAlH₄ is suspended in a mixture of 100 ml of ethyl ether and 50 ml of tetrahydrofuran. 7 g of the cyanamide, prepared above, in 40 ml of ethyl ether and 10 ml of tetrahydrofuran is added dropwise to the LiAlH₄ suspension. The resulting mixture is heated under reflux for five hours. After cooling, the excess LiAlH₄ is decomposed by treatment with a saturated aqueous solution of Na₂SO₄. A solution of sulfuric acid is added to acidify the mixture. Following decantation, the solvents in the organic phase are removed by evaporation. The resulting viscous residue is triturated several times in ethyl ether, and then treated with a solution of ammonia. The insoluble material is extracted with ethyl ether. Following washing and drying, the ether is removed by evaporation. 2.5 g of the compound of Example 4 is obtained.

EXAMPLE 5

Synthesis of the hydrochloride of N-phenoxyethyl-2-[(2-iso-propyl-4-methoxy-5-methyl)phenoxy]ethylamine or COR 28 010. 2.5 g of the product of Example 4 is dissolved in 50 ml of ether, and then gaseous HCl is bubbled through the solution. 1.7 g of the compound of Example 5 is obtained as a white powder.

EXAMPLE 6

Synthesis of 4-[N-(2,6-dimethoxyphenoxyethyl)-N-methylaminoethoxy]-5-isopropyl-2-methylphenol (formula I with $R_1 = H$, $R_2 = CH_3$,

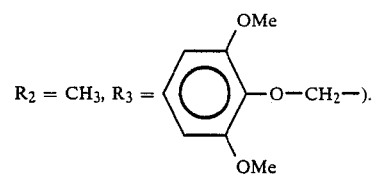

23 g of 5-isopropyl-2-methyl-4-N-methylaminoethoxyphenol is dissolved in a mixture of 200 ml of benzene and 30 ml of triethylamine and then 47 g of 47 g of 2,6-dimethoxyphenoxyacetyl chloride dissolved in 100 ml of benzene is added dropwise. The reaction mixture is heated at 50° C. for 2 hours. The benzene is removed by evaporation in a rotary evaporator, and the resulting residue is treated with a 2N HCl solution. The insoluble material is extracted twice with 150 ml of chloroform. The chloroform phase is washed and dried, and the chloroform is removed by evaporation. One obtains in this manner 63 g of 8.4 g of LiAlH₄ is suspended in a mixture of 500 ml of ethyl ether and 200 ml of tetrahydrofuran. A solution of 62 g of the product, prepared above, in 100 ml of tetrahydrofuran is added dropwise to the LiAlH₄ suspension. The resulting mixture is refluxed for 3 hours. After cooling, the excess LiAlH₄ is decomposed by treatment with a saturated aqueous solution of Na₂SO₄. The solution is acidified with a solution of sulfuric acid. The organic phase is separated and the organic solvents are removed by evaporation. The residue is triturated several times in ethyl ether, and then treated with an ammonia solution. The precipitate is extracted twice with 250 ml of chloroform. The chloroform phase is washed and dried. The chloroform is removed by evaporation, and 35 g of the compound of Example 6 is obtained.

EXAMPLE 7

Synthesis of the hydrochloride of 4-[N-(2,6-dimethoxyphenoxyethyl)-N-methylaminoethoxy]-5-isopropyl-2-methylphenol or COR 28 22.

To 10 g of the product of Example 6 dissolved in a mixture of 200 ml of diethyl ether and 50 ml of chloroform is added 50 ml of diethyl ether saturated with gaseous hydrochloric acid. The precipitate that is formed is filtered and washed with diethyl ether. One obtains 10 g of the product of Example 7, MP=161° C.

EXAMPLE 8

Synthesis of N-(2,6-dimethyoxyphenoxyethyl)-N-methyl-2-[(2-isopropyl-4-methoxy-5-methyl)phenoxy]ethylamine (formula I with $R_1 = CH_3$, $R_2 = CH_3$, $R_3 =$ A solution of diazomethane in ether is added in small portions and with stirring to a solution of 26 g of the product of Example 6 in 200 ml of ether. The excess of diazomethane is controlled by means of acetic acid. When the reaction is complete, the excess diazomethane is decomposed by adding acetic acid. The ether is removed by evaporation. The product is purified by chromatography on a silica column according to the following conditions: 16 g of the crude product is dissolved in the minimum amount of toluene. A column containing 200 g of MErck Kieselgur 60 silica in toluene was used. The elution is effected with two liters of toluene and then a 99 to 1 V/V mixture of toluenemethanol. One obtains 7 g of the compound of Example 8.

EXAMPLE 9

Synthesis of the hydrochloride of N-(2,6-dimethoxyphenoxyethyl)-N-methyl-2-[(2-isopropyl-4-methoxy-5-methyl)phenoxy]ethylamine or COR 28 11.

7 g of the product of Example 8 is dissolved in 100 ml of ethyl ether. After cooling, gaseous HCl is bubbled through. The slid is filtered and washed with a small amount of cold ethyl ether. One obtains 7 g of the compound of Examsple 9, MP=97° C.

EXAMPLE 10

Synthesis of 4-[N-(2,6-dimethoxyphenoxyethyl)aminoethoxy]-5-isopropyl-2-methylphenol (compound of formula I with $R_1=H$, $R_2=H$,

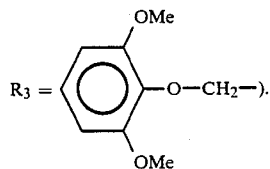

To a solution of 8 g of BrCN in 110 ml of benzene is added dropwise at room temperature a solution of 20 g of 4-[N-(2,6-dimethoxyphenoxyethyl)-N-methylaminoethoxy]-5-isopropyl-2-methylphenol in 80 ml of benzene. The mixture is heated at 50° C. for 3 hours. The benzene is removed by evaporation, and the residue is purified by extraction with hot ethyl ether. The ether is removed by evaporation and one obtains 10 g of a product of the formula

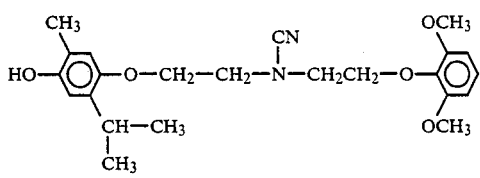

This derivative is checked by thin layer chromatography on silica using as eluant 90% chloroform-10% methanol. A solution of 10 g of the product in 100 ml of tetrahydrofuran is added dropwise to a suspension of 1.9 g of LiAlH$_4$ in 100 ml of ether. The mixture is refluxed for 5 hours. After cooling, the excess LiAlH$_4$ is decomposed by treatment with an aqueous saturated solution of Na$_2$SO$_4$. The mixture is treated according to the method described for Example 4 to obtain the compound of Example 10.

EXAMPLE 11

Synthesis of the hydrochloride of 4-[N-(2,6-dimethoxyphenoxyethyl)aminoethoxy]-5-isopropyl-2-methylphenol or COR 28 25. 3 g of the product of Example 10 is dissolved in 100 ml of ethyl ether and then gaseous HCl is bubbled through the solution. The precipitate that forms is washed with cold ether. One obtains the compound of Example 11, MP=118° C.

EXAMPLE 12

Synthesis of N-[(4-hydroxy-2-isopropyl-5-methyl)phenoxyethyl]-N-methyl-[2-(1,4-benzodioxane)]methylamine (formula I with $R_1=H$, $R_2=CH_3$,

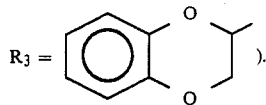

One dissolves 40.1 g of 5-isopropyl-2-methyl-4-N-methylaminoethoxyphenol in a mixture of 350 ml of benzene and 75 ml of triethylamine. A solution of 76.5 g of 2-(1,4-benzodioxane)carboxylic acid chloride in 150 ml of benzene is added dropwise. The reaction mixture is heated at 50° C. for two hours. The benzene is removed by evaporation in a rotary evaporator, and the resulting residue is trreated with a 2N HCl solution. The insoluble fraction is extracted twice with 200 ml of chloroform. The chloroform phase is washed, dried, and then the chloroform is removed by evaporation. One obtains 99 g of the compound of the formula

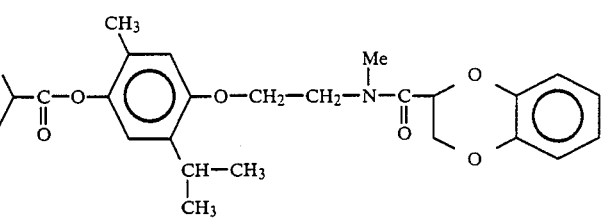

as a beige-colored solid.

To a suspension of 7.6 g of LiAlH$_4$ in a mixture of 500 ml of ethyl ether and 200 ml of tetrahydrofuran is added dropwise a solution of 53 g of the compound prepared above in 100 ml of tetrahydrofuran. The resulting mixture is refluxed for 3 hours. After cooling, the excess LiAlH$_4$ is decomposed by adding a saturated aqueous solution of Na$_2$SO$_4$. Acidification is then accomplished by adding a solution of sulfuric acid. The organic phase is separated, and then the solvent is removed by evaporation. The viscous residue is triturated several times in ethyl ether, and then treated with a solution of ammonia. The insoluble fraction is extracted twice with 150 ml of ethyl ether. The ether phase is washed, dried, and then the ether is removed by evaporation. One obtains 33.5 g of the compound of Example 12.

EXAMPLE 13

Synthesis of the hydrochloride of N-[(4-hydroxy-2-isopropyl-5-methyl)phenoxyethyl]-N-methyl-[2-(1,4-benzodioxane)]methylamine or COR 28 012.

5 g of the product of Example 12 is dissolved in 100 ml of ethyl ether and then gaseous hydrogen chloride is bubbled through. The resulting solid is filtered and washed with a small amount of cold ether.

EXAMPLE 14

Synthesis of the hydrochloride of N-[(4-acetoxy-2-isopropyl-5-methyl)phenoxyethyl]-N-methyl-[2-(1,4- benzodioxane)]methylamine (formula I with $R_1 = COCH_3$, $R_2 = CH_3$,

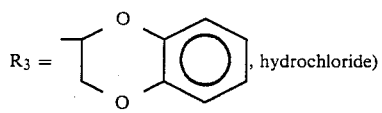, hydrochloride)

or COR 28 103.

5 g of the product of Example 12 is dissolved in a mixture of 25 g of acetic anhydride and 3.16 g of pyridine. The mixture is refluxed for 1-½ hours. Most of the pyridine and acetic anhydride are removed under vacuum. The residue is treated with a few ml of water and the resulting mixture is made basic with ammonia. An ether extraction is carried out. The organic phase is / washed, dried, and then the solvent is removed by evaporation. The resulting product is dissolved in 70 ml of ethyl ether. Gaseous hydrogen chloride is bubbled through and the precipitate that forms is filtered and washed with ethyl ether. 3.5 g of the compound of Example 14 is obtained as a beige-colored solid.

EXAMPLE 15

Synthesis of N-[(4-hydroxy-2-isopropyl-5-methyl)-phenoxyethyl]-[2-(1,4-benzodioxane)]methyl amine (compound I with $R_1$ = H, $R_2$ = H, $R_3$ =

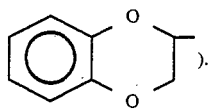).

A room temperature solution of 56 g of the product of Example 12 in 80 ml of benzene is added dropwise to a solution of BrCN in 49 ml of benzene. The resulting mixture is heated for two hours at 50° C. The benzene is removed by evaporation in a rotary evaporator, and the resulting residue is treated with 100 ml of 2N HCl. The insoluble phase is extracted twice with 150 ml of CHCl$_3$. After washing and drying, the chloroform is removed by evaporation. One obtains 55 g of the derivative

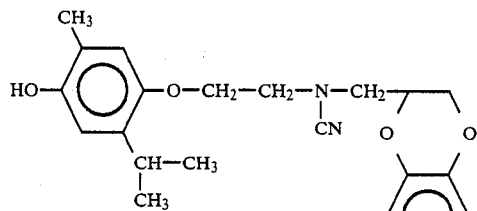

11 g of LiAlH$_4$ is suspended in a mixture of 500 ml of ethyl ether and 300 ml of tetrahydrofuran. 55 g of the above cyanamide is dissolved in 100 ml of tetrahydrofuran and then added dropwise to the LiAlH$_4$ suspension. The resulting mixture is refluxed for 3 hours. Upon cooling, the excess LiAlH$_4$ is decomposed by treatment with a saturated aqueous solution of Na$_2$SO$_4$, and then acidification with a solution of sulfuric acid is carried out. Following decantation, the solvents in the organic phase are removed by evaporation. The viscous residue is triturated several times in ethyl ether and then treated with a solution of ammonia. The insoluble phase is extracted twice with 150 ml of ethyl ether. After washing and drying, the ether is removed by evaporation. One obtains 30 g of the compound of Example 15. Thin Layer Chromatographic Control. Solvent MeOH/CHCl$_3$ 5/95 V/V Developer FeCl$_3$-K$_3$Fe(CN)$_6$ Hexachloroplatinic acid

EXAMPLE 16

Synthesis of the hydrochloride of N-[(4-hydroxy-2-isopropyl-5-methyl)phenoxyethyl]-[2-(1,4-benzodioxane)]methylamine or COR 28 14.

Gaseous hydrogen chloride is bubbled through an ethyl ether solution of 10 g of the product of Example 15. Filtration followed by washing with a small amount of cold ethyl ether results in the isolation of 10 g of the compound of Example 16.

EXAMPLE 17

Synthesis of 5-isopropyl-2-methyl-4-[N-methyl-N-(3-phenylpropyl)aminoethoxy]phenol (formula I with $R_1 = H$, $R_2 = CH_3$, $R_3 = $ 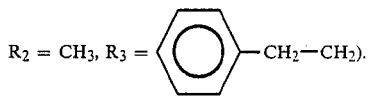).

To a solution of 44.6 g of 4-isopropyl-2-methyl-4-N-methylaminoethoxyphenol in a mixture of 350 ml of benzene and 80 ml of triethylamine is added dropwise a solution of 76 g of 3-phenylpropionyl chloride in 150 ml of benzene. The resulting mixture is refluxed for 4 hours. After evaporating the solvent, the residue is treated with a 2N solution of hydrochloric acid. The residue is extracted twice with 200 ml of chloroform. The chloroform phase is washed until it is neutral, dried with anhydrous sodium sulfate and then the solvent is evaporated. One obtains 95 g of the compound of the formula

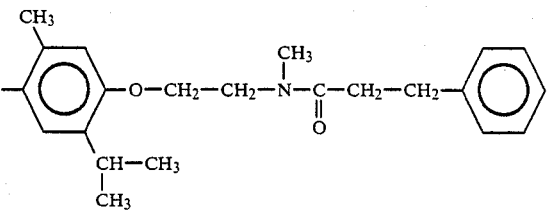

To a suspension of 19.4 g of LiAlH$_4$ in 750 m of anhydrous ethyl ether is added dropwise a solution of 95 g of the product prepared above in 250 ml of anhydrous ethyl ether. The reaction mixture is refluxed for 6 hours, and then cooled in an ice-cold water bath. The excess of LiAlH$_4$ is decomposed by addition of a saturated aqueous solution of Na2SO4. The reaction mixture is added to 1.5 liter of crushed ice containing 130 ml of concentrated H2SO4. After stirring and decanting one obtains 3 phases (an ether phase, an intermediate organic phase and an aqueous phase). The intermediate organic phase is separated by decanting and then it is made alkaline by addition of a solution of ammonia. This alkaline solution is extracted twice with 200 ml of chloroform. The chloroform phase is washed until it is neutral, dried with anhydrous sodium sulfate and then subjected to evaporation. One obtains 55.5 g of the compound of Example 17.

EXAMPLE 18

Synthesis of the hydrochloride of 5-isopropyl-2-methyl-4-[N-methyl-N-(3-phenylpropyl)aminoethoxy]-phenol or COR 28 23.

50 ml of ethyl ether saturated with gaseous hydrogen chloride is added to a solution of 8 g of the product of Example 17 dissolved in a mixture of 200 ml of ethyl ether and 50 ml of chloroform. The precipitate that forms is filtered and washed with ethyl ether. One obtains 8 g of the compound of Example 18.

EXAMPLE 19

Synthesis of 5-isopropyl-2-methyl-4-[N-(3-propylphenyl)aminoethoxy]phenol (formula I with $R_1=H$, $R_2 = H$, $R_3 =$ 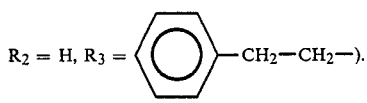 $-CH_2-CH_2-$).

A solution of 31 g of the product of Example 17 in 80 ml of benzene is added dropwise to a solution of 10.6 g of BrCN in 38 ml of benzene. The mixture is heated to 50° C. for 3 hours. After evaporation of the benzene, the residue is treated with a dilute solution of hydrochloric acid. This acid solution is extracted twice with 100 ml of ethyl ether. The ether phase is washed until it is neutral, dried with anhydrous sodium sulfate and then subjected to evaporation. One obtains 20 g of the derivative

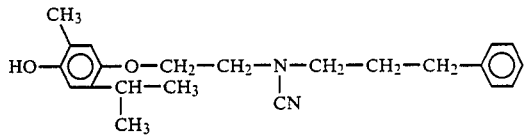

A solution of 30 g of this derivative in 100 ml of anhydrous ethyl ether is added dropwise to a suspension of 6.5 g of LiAlH4 in 300 ml of anhydrous ethyl ether. The reaction mixture is refluxed for 8 hours, and then cooled in an ice-cold water bath. The excess of LiAlH4 is decomposed by addition of a saturated aqueous solution of Na2SO4. The resulting mixture is added to 0.5 l of crushed ice that contains 25 ml of concentrated sulfuric acid. After stirring and decanting, one obtains 3 phases. The intermediate organic phase is separated by decanting and then made alkaline by addition of a solution of ammonia. This alkaline solution is extracted twice with 100 ml of ethyl ether. The ether phase is washed until it is neutral, dried with anhydrous sodium sulfate and then subjected to evaporation. One obtains 21.2 g of the compound of Example 19. This compound is purified on a silica column.

EXAMPLE 20

Synthesis of the hydrochloride of 5-isopropyl-2-methyl-4-[N-(3-phenylpropyl)aminoethoxy]phenol or COR 28 21.

To 7.9 g of the product of Example 19 dissolved in 100 ml of ethyl ether is added a small amount of ethyl ether saturated with gaseous hydrogen chloride. The precipitate is filtered and washed with ethyl ether. One obtains 7.5 g of the compound of Example 20. This compound melts between 60° and 80° C.

The following tables give the NMR spectra of the compounds described in the examples.

| | | NMR OF HYDROCHLORIDE, TMS AS INTERNAL STANDARD | | | | | | |
|---|---|---|---|---|---|---|---|---|
| | | PROTONS | | | | | | |
| Product # | Solvent | | | | Aromatic Protons | OH | Protons N+ | Other Protons |
| COR 28 09 | DMSOD6 | 6H;d; 1.2 ppm | 3H;s; 2.1 ppm | | 7H;cp; 6.6–7.6 ppm | | 1H;d6mc; 12.0 ppm | 15H;cp;2.7–4.8 ppm;CH3O— at 3.7 ppm |
| COR 28 10 | CDCl3 | 6H;d;l; 2 ppm | 3H;s; 2.2 ppm | | 7H;cp; 6.6–7.5 ppm | | 2H; broad; 10 ppm | 12H;cp;2.9–4.6 ppm; CH3O— at 3.8 ppm |
| COR 28 11 | CDCl3 | 6H;d; 1.2 ppm | 3H;s; 2.2 ppm | | 5H;cp; 6.4–7.2 ppm | | 1H; broad; 12.7 ppm | 21H;cp;3.1–4.7 ppm |
| COR 28 12 | DMSOD6 | 6H;d; 1.1 ppm | 3H;s; 2.1 ppm | | 6H;cp; 6.6–7.0 ppm | 1H;bp; 8.8 ppm | 1H; broad 11.7 ppm | 13H;cp;2.7–5.3 ppm |
| COR 28 13 | CDCl3 | 6H;d; 1.1 ppm | 3H;s; 2.1 ppm | 3H;s; 2.3 ppm | 6H;cp; 6.7–7.0 ppm | | 1H;very broadened peak; 11-13 ppm | 13H;cp;2.9–5.4 ppm |
| COR 28 14 | DMSOD6 | 6H;d; 1.1 ppm | 3H;s; 2.1 ppm | | 6H;cp; 6.6–7.0 ppm | 1H; broad; 8.9 ppm | 2H; broad; 9.9 ppm | 10H;cp;3.0–5.1 ppm |
| COR 28 21 | CDCl3 + 4 drops DMSOD6 | 6H;d; 1.1 ppm | 3H;s; 2.1 ppm | | 2H;s; 6.6 & 6.7 ppm phenol 5H;7.1 ppm | 1H; broad; 8.1 ppm | 2H; broad; 9.6 ppm | 9H;cp;1.9–3.5 ppm 2H;triplet; 4.2 ppm OCH2 |

-continued

NMR OF HYDROCHLORIDE, TMS AS INTERNAL STANDARD

| Product # | Solvent | | | PROTONS Aromatic Protons | OH | Protons N+ | Other Protons |
|---|---|---|---|---|---|---|---|
| COR 28 22 | DMSOD$_6$ | 6H;d,1 1 ppm | 3H;s; 1 ppm | ($C_6H_5$) 5H;cp; 6.5–7.2 ppm | 1H; broad; 8.9 ppm | 1H; broad; 11.4 ppm | 18H;cp;2.9– 4.6 ppm |
| COR 28 23 | CDCl$_3$ + 5 drops DMSOD$_6$ | 6H;d; 1.1 ppm | 3H;s; 2.1 ppm | 2H;s;6, 6.5–6.7 ppm phenol 5H;7.1 ppm ($C_6H_5$) | 1H; strong peak 8.2 ppm | 1H; broad 12 ppm | 12H;cp;2.0– 3.7 ppm 2H;triplet; 4.3 ppm OCH$_2$ |
| COR 28 25 | CDCl$_3$ + DMSOD$_6$ 50/50 | 6H;d; 1.1 ppm | 3H;s; 2.1 ppm | 5H;cp; 6.4– 7.2 ppm | 1H;very broad- ened peak; 7-10 ppm | 2H; strong peak; 9.3 ppm | 15H;cp;3.0– 4.5 ppm; CH$_3$O at 3.8 ppm | d = doublet; s = singlet; cp = complex pattern; bp = broadend peak

NMR of Free Bases, TMS as Internal Standard, CDCl$_3$ Solvent

| Compounds in Examples | C(CH$_3$)$_2$ | CH | NCH$_3$ | OH | Aromatic Protons | Other Protons |
|---|---|---|---|---|---|---|
| 1 | 6H;d; 1.1 ppm | 3H;s; 2.2 ppm | 3H;s; 2.5 ppm | 1H;broad; 5.5 ppm | 7H;cp;6,5– 7.4 ppm | 9H;cp;2.8– 4.3 ppm |
| 4 | 6H;d; 1.2 ppm | 3H;s; 2.2 ppm | | | 7H;cp;6.5– 7.5 ppm | 13H;cp;2.7– 4.3 ppm CH$_3$O at 3.8 ppm |
| 6 | 6H;d; 1.1 ppm | 3H;s; 2.2 ppm | 3H;s; 2.5 ppm | 1H;broad; 5.9 ppm | 5H;cp;6,4– 7.2 ppm | 15H;cp;2,8– 4.3 ppm 2CH$_3$O at 3.8 ppm |
| 12 | 6H;d; 1.1 ppm | 3H;s; 2.2 ppm | 3H;s; 2.4 ppm | 1H;broad; 5.9 ppm | 6H;cp;6.4– 7.0 ppm | 10H;cp;2.7– 4.5 ppm |
| 15 | 6H;d; 1.2 ppm | 3H;s; 2.2 ppm | | In the cp at 2.8– 4-5 ppm | 6H;cp;6.4– 7.0 ppm | 12H;cp;2.8– 4.5 ppm | d = doublet; s = singlet; cp = complex pattern

The toxicity of the compounds described in the present invention was determined by performing tests with Swiss mice. The animals, free of specific pathogenic organisms, are kept in an air-conditioned room for 24 to 48 hours before the beginning of the experiment. The animals are divided into groups consisting of 5 males and 5 females. The substances are administered with the appropriate carrier in a volume corresponding to 0.1 ml per 10 g of animal weight.

The following tables display the LD 50 determined for each compound, for oral and intraperitoneal administration, by utilizing the method described by J. C. Cazin (Bull. Soc. Pharm. Lille, 1972, 4, 187). In case the LD 50 could not be measured, the mortality percentages produced by various doses are reported.

ORAL ADMINISTRATION

| Compound | Solvent | Dose in mg/kg | Percentage mortality | Ld 50 in mg/kg |
|---|---|---|---|---|
| COR 28 09 | water | 1000 2000 | 0 | |
| COR 28 10 | gum arabic | 1000 | 20 | |
| COR 28 11 | gum arabic | | | 546(377–791) |
| COR 28 12 | DMSO ½ | | | 1428(1261–1617) |
| COR 28 13 | DMSO ½ | 1000 2000 | 0 20 | |
| COR 28 14 | DMSO ½ | | | 952(790–1148) |
| COR 28 21 | Tween | | | 358.6(300.4–428.1) |
| COR 28 22 | Tween | | | 316(253–396) |
| COR 28 23 | Tween | | | 615.3(527.8–717.3) |

ORAL ADMINISTRATION -continued

| Compound | Solvent | Dose in mg/kg | Percentage mortality | Ld 50 in mg/kg |
|---|---|---|---|---|
| Moxisylyte | gum arabic | | | 225(227–286) |

DMSO = dimethylsulfoxide

INTRAPERITONEAL ADMINISTRATION

| Compound | Solvent | Ld 50 mg/kg |
|---|---|---|
| COR 28 09 | DMSO ½ | 200(188–212) |
| COR 28 10 | water | 81(65–100) |
| COR 28 11 | water | 93(72–120) |
| COR 28 12 | DMSO ½ | 350 |
| COR 28 13 | DMSO ½ | 600(463–778) |
| COR 28 14 | DMSO ½ | 174(151–200) |
| COR 28 21 | Tween | 84.6(80.2–89.3) |
| COR 28 22 | Tween | 66.2(60.7–72.3) |
| COR 28 23 | Tween | 154(125.3–189.6) |
| Moxisylyte | Physiological serum | 73(67–79) |

In vitro alpha-blocking activity is determined by the antagonism of contractions of aortic strips isolated from rabbits. The contractions are induced by noradrenaline at a concentration of $2 \times 10^{-6}$ M/l. The technique utilized is derived from that of Furchgott and Bhadrakom (J. Pharmacol., 1953, 108, 129–43). The agonist is introduced in the bath 30 seconds or 14 minutes after the addition of the antagonist. The following table gives the values of CI 50 expressed in M/l, that is, the concentrations of alpha-blocking compounds that result in a 50% inhibition of the standard contraction induced by the noradrenaline.

| Compound | CI 50 M/l |
|---|---|
| COR 28 09 | $2.6 \cdot 10^{-4}$ |
| COR 28 10 | $3.5 \cdot 10^{-4}$ |
| COR 28 11 | $2.16 \cdot 10^{-5}$* |
| COR 28 12 | $9 \cdot 10^{-5}$ |
| COR 28 13 | $2.52 \cdot 10^{-4}$ |
| COR 28 14 | $6 \cdot 10^{-6}$ |
| COR 28 21 | $1.17 \cdot 10^{-5}$ |
| COR 28 22 | $1.78 \cdot 10^{-7}$ |
| COR 28 23 | $2.70 \cdot 10^{-6}$ |
| COR 28 35 | $8.36 \cdot 10^{-7}$ |
| Moxisylyte | $1.7 \cdot 10^{-5}$ |

*Contact time 14 min

The in vivo alpha-blocking activity is estimated by the measurement of the antagonism of hypertension induced by phenylephrine. For intravenous administration, amyelic rats with both vagus nerves removed according to the technique of J. S. Gillespie and T. C. Muir (Br. J. Pharmac. Chemother., 1967, 30, 78–87) are used. The alpha-blocking agents are administered at doses of 0.2, 1.6 and 3.2 mg/kg. The percentage inhibition of the maximum activity and the time for the residual activity to become 50% of the maximum activity are measured. The results are presented in the following table.

in the jugular vein are used. Compound COR 28 11 results in a maximum activity of $56.7 \pm 10.25\%$ at a dose of 5 mg/kg. After 60 minutes, the activity is still 30%. The antihypertensive activity is determined on rats of Okamoto stock that are spontaneously hypertensive and anesthesized with pentobarbital. A dose of 0.1 mg/kg of compound COR 28 11 administered intravenously causes the average blood pressure to go from 135 to 106 mm of mercury.

The activity in preventing the aggregation of platelets was revealed by utilizing unwashed human platelets of normal adult individuals. The studies were carried out with platelets in their natural surroundings (plasma rich in platelets). The inhibiting agent was tested in the presence of four types of aggregating agents (ADP, adrenalin, collagen, arachidonic acid) at various concentrations.

For each case, a dose-response curve was established. The inhibiting power is characterized by the dose that corresponds to 50% inhibition, symbolized as I 50.

In the following table are reported, for some of the compounds in the present invention, values of I 50 expressed in M/l with respect to the four aggregating agents and in comparison to ticlopidine taken as reference.

| | Product tested | | |
|---|---|---|---|
| | Formula I with $R_1 = CH_3$ $R_2 = CH_3$ $R_3 =$ 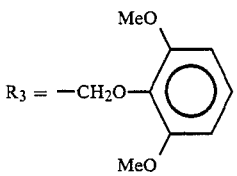 | Formula I with $R_1 = H$ $R_2 = H$ $R_3 =$ 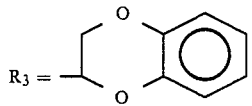 | Ticlopidine |
| Aggregating agent | | | |
| ADP 1.25µM/l | $7 \cdot 10^{-5}$ | $6 \cdot 10^{-5}$ | $10^{-5}$ |
| ADP 2.5µM/l | $7.4 \cdot 10^{-5}$ | $5.8 \cdot 10^{-5}$ | $5 \cdot 10^{-5}$ |
| adrenalin 1µM/l | $1.6 \cdot 10^{-5}$ | $2.4 \cdot 10^{-5}$ | $3.7 \cdot 10^{-5}$ |
| adrenalin 5µM/l | $4 \cdot 10^{-5}$ | $5 \cdot 10^{-5}$ | $5.2 \cdot 10^{-5}$ |
| collagen 50µg/ml | $10^{-4}$ | $5.2 \cdot 10^{-5}$ | $>10^{-4}$ |
| arachidonic acid | | | |
| $5 \cdot 10^{-4}$ M/l | $>10^{-4}$ | $1.5 \cdot 10^{-5}$ | |
| $10^{-3}$ M/l | $>10^{-4}$ | $5.4 \cdot 10^{-5}$ | |

Taking into consideration their pharmacological properties, namely, alpha-blocking and antihypertensive activities, the compounds described in the present invention can be utilized, for example, in the treatment of arterial hypertension (either the compounds alone or

| | 0.2 mg/kg | | 1.6 mg/kg | | 3.2 mg.kg | |
|---|---|---|---|---|---|---|
| Compound | % of maximum activity | time in min. | % of maximum activity | time in min. | % of maximum activity | time in min. |
| COR 28 09 | | | $51.4 \pm 5.10$ | 4 m 29 s | $74.7 \pm 5.2$ | 7 m 20 s |
| COR 28 10 | | | $66.3 \pm 1.83$ | 5 m 33 s | 77 | 12 m 44 s |
| COR 28 11 | | | $61.8 \pm 4.90$ | >60 m | $74.60 \pm 4.4$ | 60 m |
| COR 28 12 | | | $59.1 \pm 7.50$ | 5 m 53 s | $65.7 \pm 4.5$ | 6 m 16 s |
| COR 28 13 | | | $46.1 \pm 6.01$ | 5 m .40 s | $61.1 \pm 6.4$ | 9 m 9 s |
| COR 28 14 | | | $92.0 \pm 2.45$ | 26 m 2 s | $100 \pm 0$ | >60 m |
| COR 28 21 | | | $73.44 \pm 6.99$ | 50 m | | |
| COR 28 22 | $91.12 \pm 3.46$ | 35 m | $112.48 \pm 7.3$ | 120 m | | |
| COR 28 23 | | | $81.09 \pm 2.35$ | 20 m | | |
| COR 28 25 | $70.20 \pm 4.89$ | 20 m | $94.84 \pm 2.22$ | 120 m | | |
| Moxisylyte | | | $83.1 \pm 5.71$ | 17 m .20 s | $82.6 \pm 4.54$ | 18 m 23 s |

For oral administration, male rats kept awake and fitted with catheters implanted in the carotid artery and in association with a diuretic or other antihypertensive drugs), in the treatment of peripheral vascular troubles such as acrocyanosis and Raynaud's syndrome, in the treatment of asthma attacks (either the compounds alone or in association with a beta-stimulant), and in the treatment of glaucoma.

Taking into consideration their properties in preventing the aggregation of platelets, it will be possible to utilize the compounds (alone or in association with other compounds) described in the present invention in the prophylaxis of arterial thrombotic accidents (for example, in patients with artificial heart valves, in the prevention of cerebral vascular accidents, in the prevention of myocardial infarctions). It will be possible to utilize the compounds in the present invention in association with other products, such as heparin or fibrinolytic agents, usually employed in the treatment of acute thrombosis.

The doses and therapeutic procedures will depend on the subject and the disease to be treated. It will be possible to administer the compounds orally (for example in the form of capsules, tablets, liquid drops), by injection (intramuscular or intravenous injectable solutions; administration via intravenous perfusion), via the rectum (suppositories), locally (collyria for the treatment of glaucoma, aerosols for the treatment of asthma attacks). Depending upon the circumstances, the daily dose will vary between 1 and 100 mg in one to three oral doses, between 1 and 100 mg in one or two rectal doses; the dose administered intravenously will vary between 0.1 and 10 mg. Collyria will contain 0.05 to 0.5% of the active ingredient, and the aerosols will deliver 0.1 to 10 mg of the active ingredient for each inhalation.

We claim:

1. A compound with alpha 1-blocking activity having the formula

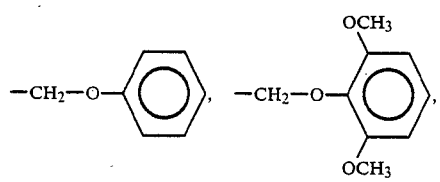

wherein $R_1$ is —H, —CH$_3$ or —COCH$_3$;
$R_2$ is —H or CH$_3$; and
$R_3$ is

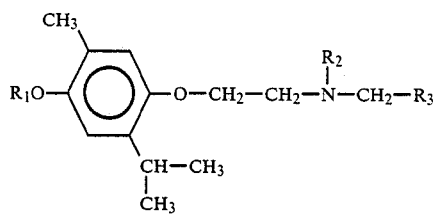

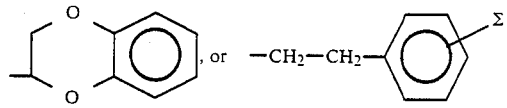

wherein $\Sigma$ is —H or one or more substituents selected from the group consisting of halogen, —OH and —OCH$_3$;
or a pharmaceutically acceptable salt thereof.

2. The compound according to claim 1, wherein $R_3$ is

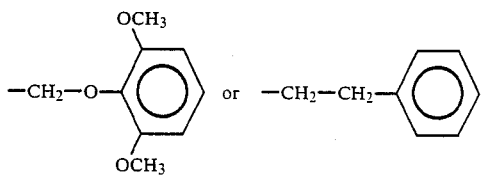

3. A pharmaceutical composition comprising with alpha 1-blocking activity a compound having the formula

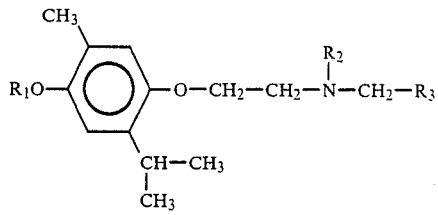

wherein $R_1$ is —H, —CH$_3$ or —COCH$_3$,
$R_2$ is —H or CH$_3$, and
$R_3$ is

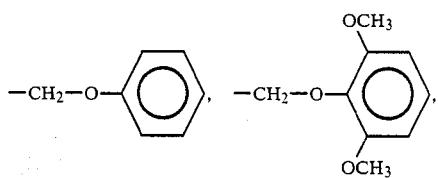

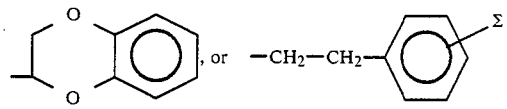

wherein $\Sigma$ is —H or one or more substituents selected from the group consisting of halogens, —OH and —OCH$_3$, or
a pharmaceutically acceptable salt thereof;
and a pharmaceutically acceptable adjuvant or diluent in the form of capsules, tablets, liquid drops, injectable solutions, suppositories, collyria or aerosols.

4. A method for blocking alpha 1 receptors in mammals which comprises administering an effective amount of a composition according to claim 3.

* * * * *

UNITED STATES PATENT AND TRADEMARK OFFICE
CERTIFICATE OF CORRECTION

PATENT NO. : 4,818,772
DATED : April 04, 1989
INVENTOR(S) : Henri Pontagnier, et al It is certified that error appears in the above-identified patent and that said Letters Patent is hereby corrected as shown below:

On the Title Page, Item [30]:
Delete the data under "Foreign Application Priority Data" and substitute --Mar. 4, 1982 [FR]   France...............82 03795--
--Mar. 4, 1982 [FR]   France...............82 03796--, therefor.

Signed and Sealed this

Twenty-eighth Day of November 1989

*Attest:*

JEFFREY M. SAMUELS

*Attesting Officer*   *Acting Commissioner of Patents and Trademarks*